(12) United States Patent
Deorsola

(10) Patent No.: US 11,234,820 B2
(45) Date of Patent: Feb. 1, 2022

(54) METHOD FOR GENERATING A MITRAL REPAIR RING, AND MITRAL REPAIR RING

(71) Applicant: CD MED S.R.L., Turin (IT)

(72) Inventor: Luca Deorsola, Turin (IT)

( * ) Notice: Subject to any disclaimer, the term of this patent is extended or adjusted under 35 U.S.C. 154(b) by 144 days.

(21) Appl. No.: 16/491,305

(22) PCT Filed: Mar. 7, 2017

(86) PCT No.: PCT/IB2017/051313
§ 371 (c)(1),
(2) Date: Sep. 5, 2019

(87) PCT Pub. No.: WO2018/162949
PCT Pub. Date: Sep. 13, 2018

(65) Prior Publication Data
US 2020/0030095 A1     Jan. 30, 2020

(51) Int. Cl.
*A61F 2/24*     (2006.01)
(52) U.S. Cl.
CPC .... *A61F 2/2445* (2013.01); *A61F 2230/0095* (2013.01); *A61F 2240/002* (2013.01)
(58) Field of Classification Search
CPC .. A61F 2/2442–2448; A61F 2230/0008; A61F 2230/0065; A61F 2230/0095; A61F 2240/001–002; A61F 2250/0059
See application file for complete search history.

(56) References Cited

U.S. PATENT DOCUMENTS

| | | | | |
|---|---|---|---|---|
| 5,972,030 | A * | 10/1999 | Garrison | A61B 17/00234 623/2.11 |
| 2008/0154359 | A1* | 6/2008 | Salgo | A61F 2/2448 623/2.36 |
| 2009/0177276 | A1* | 7/2009 | Carpentier | A61F 2/2448 623/2.36 |

FOREIGN PATENT DOCUMENTS

| | | |
|---|---|---|
| WO | 2017/011383 A1 | 1/2017 |
| WO | 2017/061956 A1 | 4/2017 |

OTHER PUBLICATIONS

Levine et al, "Three-Dimensional Echocardiographic Reconstruction of the Mitral Valve, with Implications for the Diagnosis of Mitral Valve Prolapse", (Sep. 1989), Circulation, vol. 80, No. 3, pp. 589-598. (Year: 1989).*

(Continued)

*Primary Examiner* — Paul B Prebilic
(74) *Attorney, Agent, or Firm* — Abelman, Frayne & Schwab; Stefan Knirr (57) ABSTRACT

In certain aspects, the invention relates to a method for generating a mitral repair ring for a corresponding mitral valve, comprising the steps of generating (S1) a reference circumference (13) indicative of said valve ring (110); generating (S2) a reference grid (2); inscribing (S3) said reference circumference (13) in said reference grid (2); combining (S4) said reference circumference (13) with a plurality of characteristic measures (15, 16, 17, r1-r6) of said mitral valve (100); generating (S5) a three-dimensional reference grid (250); identifying (S6) on said three-dimensional reference grid (250) a plurality of deformation points (300-302) of said reference circumference (13); deforming said reference circumference (13) at said deformation points (300-303) so as to obtain a geometric model (10) of said mitral repair ring (10'); and generating said mitral repair ring (10') from said obtained geometric model (10). The invention also relates to the mitral repair ring obtained by means of the aforesaid method and to its use in mitral annuloplasty.

16 Claims, 9 Drawing Sheets

(56) References Cited

OTHER PUBLICATIONS

International Search Report, dated Sep. 15, 2017 for corresponding PCT patent application No. PCT/IB2017/051313.
Bastian Graser et al: "Computer-Asisted Analysis of Annuloplasty Rings" BILDVERARBEITUNG fFUR DIE MED, Jan. 1, 2013, pp. 75-80, DOI: 10,1007/987-3-642-36480-8_15.

* cited by examiner

METHOD FOR GENERATING A MITRAL REPAIR RING, AND MITRAL REPAIR RING

CROSS REFERENCE TO RELATED APPLICATIONS

This application is a national phase of PCT application No. PCT/IB2017/051313, filed Mar. 7, 2017, which is incorporated herein by reference thereto.

FIELD OF THE INVENTION

The present invention relates to a method for generating a mitral repair ring adapted to be used during surgeries on the mitral valve, as well as to a mitral repair ring obtained by this method. The present invention also relates to a computer program conceived to implement the method itself.

BACKGROUND ART

The mitral valve, also known as the bicuspid valve, is one of the four heart valves. It is located at the base of the left ventricle, forming an integral part thereof. The left ventricle is the cardiac cavity which receives oxygenated blood from the left atrium, in turn received from the lungs, to pump it throughout the body's circulatory district. To perform this function, the ventricle has an inlet and an outlet provided with a valve: thereby, the blood flow is always and only moving in the right direction. The mitral valve is the inlet of the left ventricle and thus directs the blood flow. When the left ventricle dilates to receive oxygenated blood from the left atrium, the valve opens to allow the passage of blood; when the left ventricle contracts to pump the received blood, the valve closes to prevent the return of blood to the left atrium, so that the blood can only proceed towards the aorta.

As a valve, the mitral or bicuspid valve structure comprises an orifice and an obturator. The orifice is the valve ring, the perimeter of which has an approximately oval shape, the obturator instead comprises two leaflets, specifically a front leaflet and a rear leaflet, defined by a thin layer of tissue which develops from the ring valve. Two bundles of tendinous chords are connected to the front and rear leaflets to open and close them in the right direction, i.e. only towards the ventricle. Furthermore, the valve ring has a special saddled shape.

Many patients suffer from diseases or disorders typically related to anatomical impairments of the mitral valve. When the mitral valve is affected by an anatomical impairment, the shape and/or components thereof show deformations which make them different from those of a physiologically suitable valve. In order to correct these disorders, it is often necessary to resort to valve repair surgery.

When the surgeon is faced with a condition of this type, he/she carries out a preoperative echocardiographic investigation, to study the valve anatomy and identify the deformed components or anatomical portions responsible for the functionality defect. Several important measures to guide the surgeon in the repair procedure are also carried out.

The above surgery is performed under extracorporeal circulation, with an arrested and empty heart. However, the heart in vivo has shape, size and volume different than those in the conditions of a surgery. For this reason, during the surgical procedure, the valve presents a substantially different anatomy from that previously observed on echocardiography.

In other words, the surgeon operates on a "deflated" heart which in vivo, i.e. with the cardiac organ in activity, takes instead quite different shape and dimensions. As a result, the corrective actions of the surgeon on a mitral valve under these conditions inevitably are approximate. In particular, the valve is "crumpled", a condition which makes difficult the examination of the intraoperative anatomy thereof.

In many cases, the surgery provides also for the removal of damaged portions of the valve tissue and the valve reconstitution with the remaining tissue. With this technique, a reconstructed valve is obtained which, however, even if working, has a shape and/or a dimension different from the original one and, often, different from a physiological one. Despite the existence of "geometrical rules" which can guide the surgeon during the surgery, actually his/her experience and manual skill are decisive for the success of the surgery.

The surgery also provides for the placement of a stabilization ring, which the surgeon sutures to the ring valve to maintain in time the desired shape and size for the mitral valve. Various measures for these stabilization rings are available to adapt to the different sizes of the valve ring.

It is one of the main objects of the present invention to solve the disadvantages which affect the prior art in a simple and cost effective manner.

SUMMARY

The inventive idea underlying the present invention rises from a careful observation of the heart anatomy, in particular from the analysis of the ratios which characterize the portions of a physiologically acceptable mitral valve, to devise a method which allows the generation of a mitral repair ring substantially mirroring the shape and the ratios of a suitable physiologically valve to perform its function in a working heart.

In fact, it has been found that the conventional cardiac surgical techniques are inadequate to faithfully restore a mitral valve with anatomical impairment, since during the repairing surgery the heart is in cardioplegic arrest and the shape of the mitral valve does not correspond to the shape that it has when the heart is working.

The surgeon must consider this condition and try to manually compensate for the anatomical differences found. In any case, the deformability of the tissues affected by the surgery influences the restoration operations of the mitral valve physiology and functionality, which is disadvantageous.

Therefore, in a first aspect, the invention relates to a method for generating a mitral repair ring for a corresponding mitral valve;

More particularly, the method comprises the steps of:
generating a reference circumference indicative of said valve ring;
generating a reference grid;
inscribing said reference circumference in said reference grid;
combining said reference circumference with a plurality of measures characteristic of said mitral valve;
generating a three-dimensional reference grid;
identifying on said three-dimensional reference grid a plurality of deformation points of said reference circumference;
deforming said reference circumference at said deformation points to obtain a geometric model of the mitral repair ring; and generating or producing the mitral repair ring, from the obtained geometric model.

In a second aspect, the invention relates to a mitral repair ring obtained by the method according to the invention.

Advantageously, the mitral repair ring obtained with the method according to the invention has a configuration next to that of a valve ring in vivo. It is therefore capable of facilitating the surgical technique of mitral valve repair and speed up the time of the surgery, with consequent reduction of the times of use of heart-lung machines.

Furthermore, the use of the repair mitral ring according to the invention considerably reduces the risks of reconstructing the mitral valve with a shape and/or size substantially different from those of the same mitral valve observed on echocardiography when the heart is beating.

Finally, in a further aspect, the present invention relates to a computer program. More particularly, the computer program is loadable on the memory of a computer and executable by a relative processor unit, comprising a suitable code to perform the steps of the above method.

BRIEF DESCRIPTION OF THE DRAWINGS

Further features and advantages of the method for generating a mitral repair ring and of the mitral repair ring itself according to the present invention will become apparent from the following detailed description of some preferred embodiments, given below by way of non-limiting example, with reference to the accompanying drawings.

In the drawings.

DETAILED DESCRIPTION OF THE INVENTION

Figure 1:
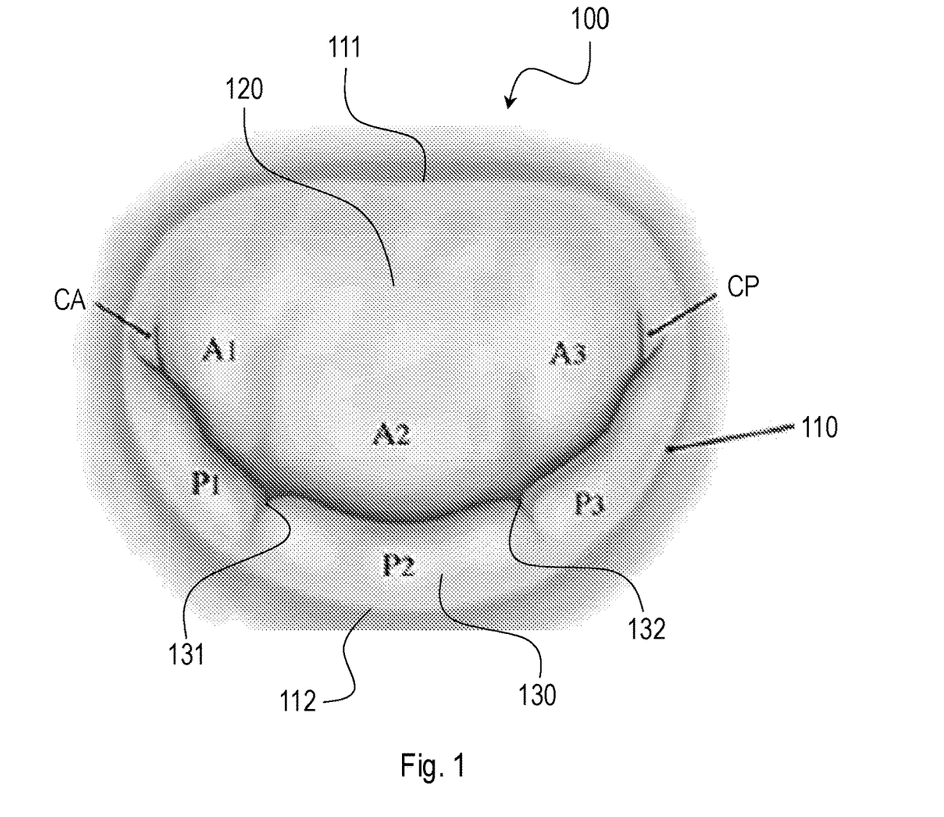
FIG. 1 schematically shows the structure of a mitral valve.

With reference to FIG. 1, a mitral valve, generally indicated by the reference numeral 100, is schematically shown.

The mitral valve 100 includes a valve ring 110 and a pair of leaflets, namely a front leaflet 120 and a rear leaflet 130, opening and closing the valve ring 110.

More in particular, the front leaflet 120 has a semi-circular shape and occupies two fifths of the entire annular circumference, while the rear leaflet 130 has a substantially quadrangular shape and is attached to three-fifths of the annular circumference.

The valve ring 110 is thus divided into a front portion, or front ring 111, occupied by the front valve leaflet 120, and a rear portion, or rear ring 112, occupied by the rear valve leaflet 130.

The front 120 and rear 130 valve leaflets are joined together, and to the ring valve 110, at two areas, referred to as the front commissure CA and the rear commissure CP, respectively.

The free edge of the front 120 and rear 130 valve leaflets corresponds to the edge which is not connected to the ring valve 110 and the distance between the free edge and the valve ring 110 is defined as the leaflet height. Furthermore, the contact line between the free edges of the front 120 and rear 130 valve leaflets is referred to as the coaptation line. When the mitral valve 100 is in its closed condition, shown in FIG. 1, the front 120 and rear 130 leaflets are in contact along the coaptation line (coapt), thus preventing the blood regurgitation in the left atrium.

The rear leaflet 130 also shows two typical indentations 131, 132, which divide it into three portions or scallops. In accordance with the Carpenter's nomenclature, the portions of the rear leaflet 130 are classified as anterolateral portion P1, median portion P2 and posteromedial portion P3. The front leaflet 120 does not have indentations, but it is equally divided, based on the proximity with the indentations 131, 132 of the rear leaflet 130, in an anterolateral portion A1, a median portion A2 and a posteromedial portion A3.

Figures 2, 3:
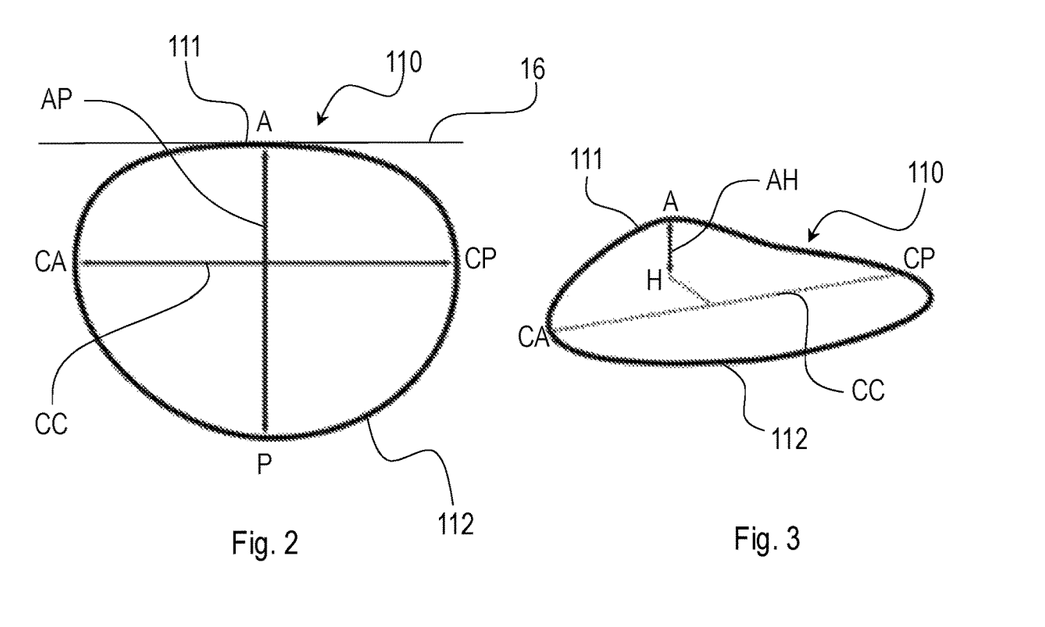
FIG. 2 is a schematic plan view of a valve ring seen from the atrial side.
FIG. 3 is a three-dimensional schematic view of the valve ring in FIG. 2.

As shown in FIG. 2, when looking at the valve ring 110 from the atrial side, it appears of an irregularly ellipsoidal shape or "in the form of a D". For this reason, its extension is characterized by its major diameters, i.e. the anteroposterior diameter AP and the commissure-commissure diameter CC.

More particularly, the anteroposterior diameter AP is the line which connects the middle point A of the front ring 111 to the middle point P of the rear ring 112; the commissure-commissure diameter CC is the line connecting the front CA and rear CP commissures.

The anteroposterior diameter AP and the commissure-commissure diameter CC are two characteristic measures of the ring valve 110.

The anterior-posterior commissure AP and the commissure-commissure CC diameters, as well as the shape of the ring valve 110, are not stable and constant but undergo considerable changes during the various phases of the cardiac cycle. In particular, during the latter phase of diastole, at the wave P of the electrocardiogram (ECG), the valve ring 110 reaches its maximum size and takes a circular shape; on the contrary, during systole, the valve area decreases with an oscillating variation between 20 and 40%, and the valve ring 110 takes an elliptical shape, with a ratio of the major to minor diameters of approximately 0.75. In a three-dimensional view, shown in FIG. 3, the valve ring 110 instead has a slightly saddled shape, or more precisely as a hyperbolic paraboloid, with the highest point, which is the most distant point from the apex of the left ventricle, located at the middle point A of the front ring 111, and the lowest point H placed instead anterolaterally and posterolaterally near to the front CA and rear CP commissures. The distance between the highest point A and the lowest point H of the ring valve 110 is referred to as the annular height AH and represents another important characteristic measure of the valve ring 110.

With reference to FIGS. 4 to 12, the method for determining a mitral repair ring 10' (FIG. 13) for a mitral valve 100 according to a preferred embodiment of the present invention is now described.

Figure 4:
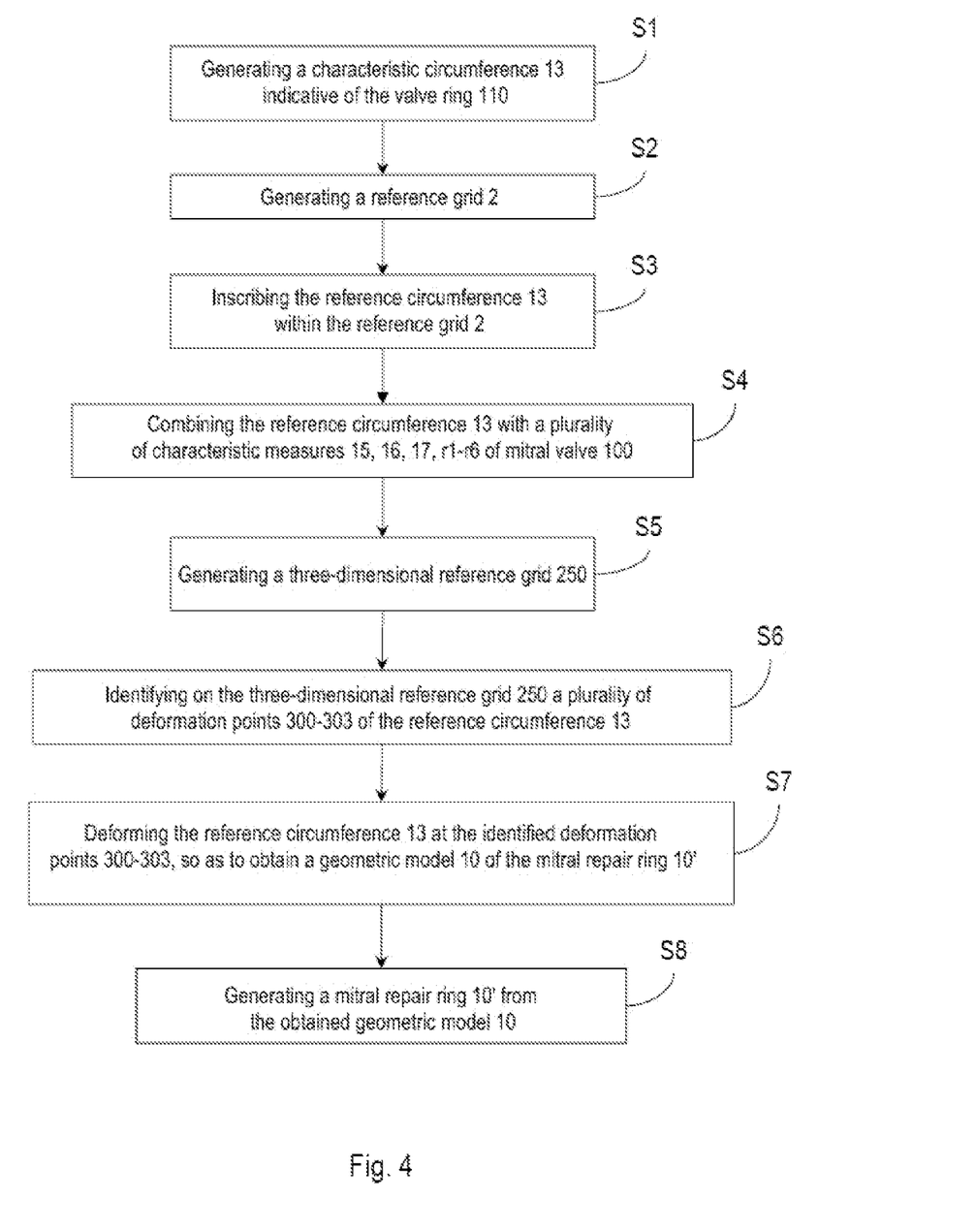
FIG. 4 is a block diagram, showing the steps of the method according to the invention.

The method comprises an initial step S1, during which a reference circumference 13, indicative of the valve ring 110, is generated.

In the embodiment of the method, shown in FIGS. 5 to 12, in order to generate the reference circumference 13, the anteroposterior diameter AP is used as a characteristic measure of the starting valve ring 110, i.e. as described above with reference to FIG. 2, the line connecting the middle point A of the front ring 111 to the middle point P of the rear ring 112 of the mitral valve 100.

Figure 5:
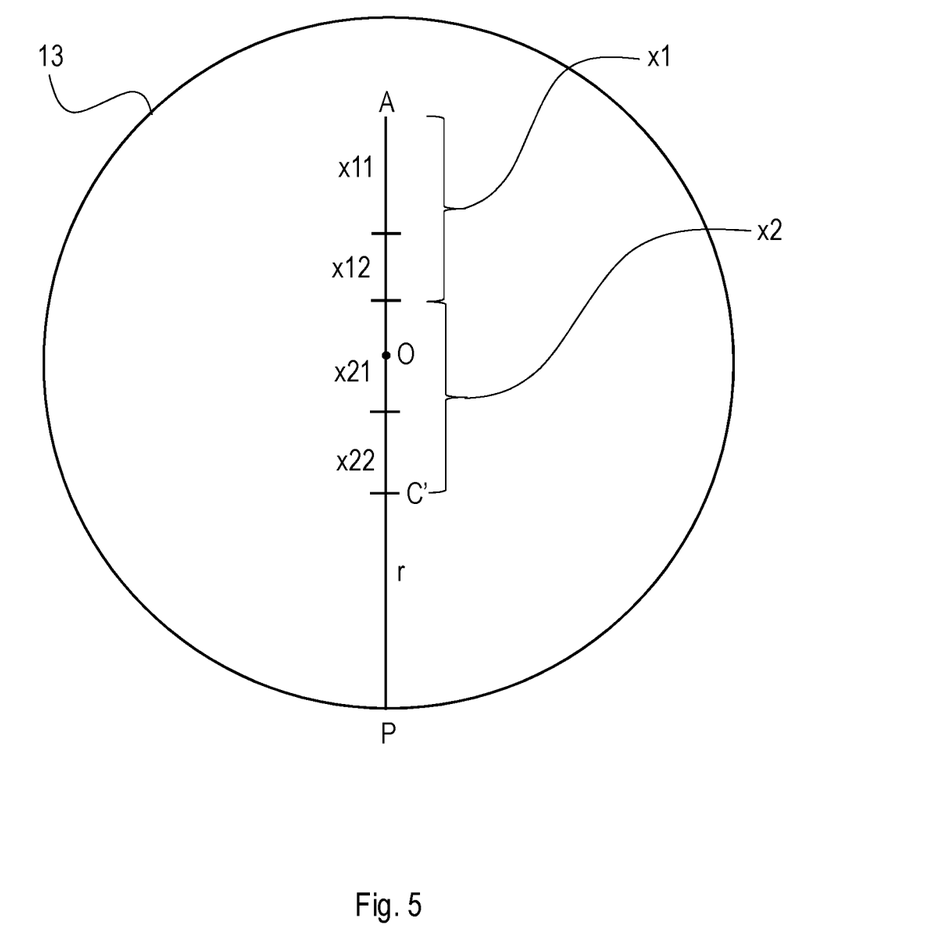
FIG. 5 shows a geometrical structure, developed according to the teachings of the present invention, for generating a reference circumference indicative of the valve ring of a mitral valve.

Thereafter, and with reference to FIG. 5, on the anteroposterior diameter AP, a point C is identified, said point of coaptation C', such that the anteroposterior diameter AP is divided into two sections, AC' and C'P respectively, in a mutual golden ratio, i.e. such that the following formula applies:

$$AC'/C'P=\phi \qquad (1)$$

where $\phi$ is the Fidia's constant, equal to 1.6180339887 . . . .

The point of coaptation C' is the point at which the anterior-posterior axis AP intersects the line of coaptation between the front 120 and rear 130 valve leaflets. Instead, coaptation axis 15 (FIG. 8) is defined a straight line passing through the point of coaptation C'. The coaptation axis 15 is a characteristic measure of the mitral valve 100. Another characteristic measure of the mitral valve 100 is the front deformation axis 16 (FIG. 2), consisting of a straight line passing through the middle point A of the front ring 111.

As a result, the AC' section represents the portion of the anteroposterior diameter AP pertaining to the front valve leaflet 120 and the C'P stretch represents the portion of the anteroposterior diameter AP pertaining to the rear valve leaflet 130. The AC' stretch is then divided into two equal segments, x1 and x2, respectively, which are in turn divided into two segments, respectively x11, x12, and x21, x22.

The x11 and x12 segments are in mutual golden ratio, i.e. related by the formula:

$$x11/x12\phi \qquad (2)$$

Similarly, the x21 and x22 segments are in mutual golden ratio, i.e. related by the formula:

$$x21/x22\phi \qquad (3)$$

in formulas (2) and (3) $\phi$ is the Fidia's constant, equal to 1.6180339887.

in formulas (2) and (3) $\phi$ is the Fidia's constant, equal to 1.6180339887 . . . .

At this point, the reference circumference 13 may be generated, which is a circumference having its centre O at the middle point of the segment x21 and radius r equal to the distance between the centre O and the middle point P of the rear ring 112.

The reference circumference 13 thus generated represents the valve ring 110 lying in a plane, i.e. not yet in its natural saddled shape.

Although the anteroposterior diameter AP of the valve ring 110 has been used above as a starting characteristic measure to generate the reference circumference 13, it is understood that the reference circumference 13 can be generated from any other characteristic measure of the valve ring 110 or the mitral valve 100, such as the transverse diameter of the valve ring 110, which corresponds to the diameter of the reference circumference 13, the maximum height AC', the height C'P of the front leaflet 120, the height C'P of the median portion P2 of the rear leaflet 130, which corresponds to the radius r of the reference circumference and which is in golden ratio with the anteroposterior diameter AP, the annular height AH which is in golden ratio with the anteroposterior diameter AP, and other characteristic measures which are suitable for the purpose.

Once the reference circumference 13 (step S1) has been determined, the method proceeds with a step S2 of generating a reference grid 2, on which the reference circumference 13 will be placed. Preferably, the reference grid 2 is a grid of a pentagonal reference, comprising a plurality of pentagons of increasingly small dimensions, inserted one inside the other.

Figure 6:
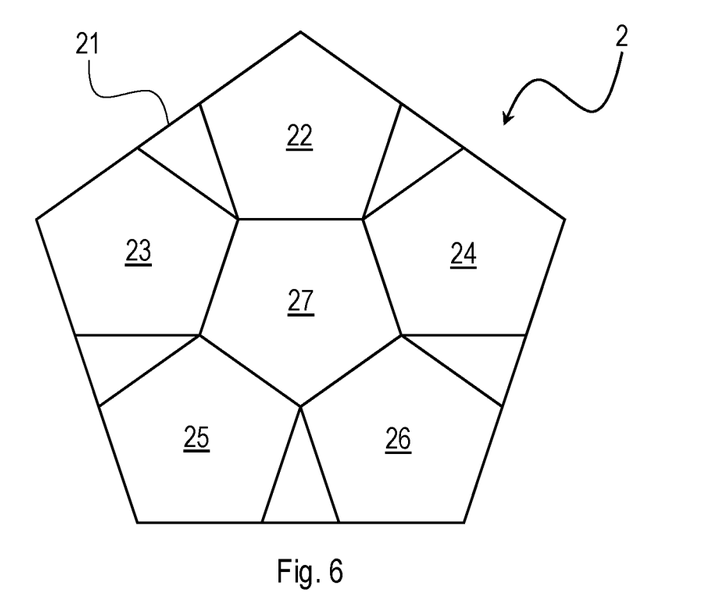
FIGS. 6 and 7 show a reference grid developed according to the teachings of the present invention.
Figure 7:
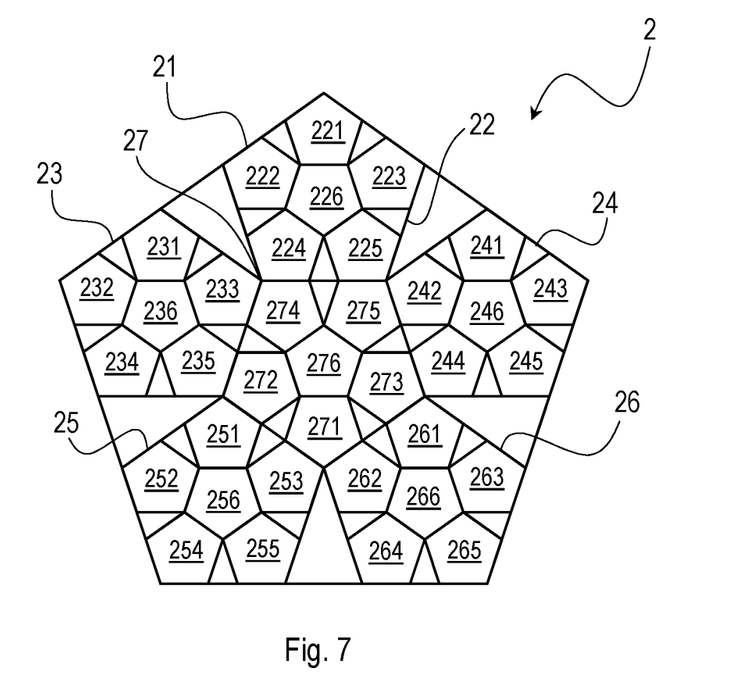

In particular, and as shown in detail in FIGS. 6 and 7, this step S2 of generating the grid 2 comprises the following sub-steps:

generating a pentagon 21, referred to as the first level pentagon, of such dimensions as to circumscribe the reference circumference 13 (not shown in FIGS. 6 and 7);

generating inside the first level pentagon 21, a number of pentagons 22-27, referred to as second level pentagons; and generating, within each second level pentagon 22-27, a number of pentagons 221-226, 231-236, 241-246, 251-256, 261-266, referred to as third level pentagons.

In particular, the second level pentagons 22-27, generated within the first level pentagon 21, comprise: a second level apical pentagon 22, two second level side pentagons 23 and 24, two second level base pentagons 25 and 26, and a second level central pentagon 27.

The second level apical pentagon 22 contains six third level pentagons therein, i.e. a third level apical pentagon 221, two third level side pentagons 222 and 223, two third level base pentagons 224 and 225, and a third level central pentagon 226.

The second level side pentagon 23 contains six third level pentagons therein, i.e. a third level apical pentagon 231, two third level side pentagons 232 and 223, two third level base pentagons 234 and 235, and a third level central pentagon 236.

The second level side pentagon 24 contains six third level pentagons therein, i.e. a third level apical pentagon 241, two third level side pentagons 242 and 243, two third level base pentagons 244 and 245, and a third level central pentagon 246.

The second level base pentagon 25 contains six third level pentagons therein, i.e. a third level apical pentagon 251, two third level side pentagons 252 and 253, two third level base pentagons 254 and 255, and a third level central pentagon 256.

The second level base pentagon 26 contains six third level pentagons therein, i.e. a third level apical pentagon 261, two third level side pentagons 262 and 263, two third level base pentagons 264 and 265, and a third level central pentagon 266.

The second level central pentagon 27 contains six third level pentagons therein, i.e. a third level apical pentagon 271, two third level side pentagons 272 and 273, two third level base pentagons 274 and 275, and a third level central pentagon 276.

Preferably, the first level 21, the second level 22-27 and the third level 221-226, 231-236, 241-246, 251-256, 261-266 and 271-276 pentagons are all regular pentagons, thus the pentagonal reference grid 2 is preferably a grid of regular pentagons.

The choice of a grid 2 of regular pentagons results from the golden ratio which characterizes the size of a regular pentagon. It is known that the ratio between one of the diagonals of a regular pentagon and one of its sides is equal to the constant of Fidia $\phi$ (~1.6180).

Figure 8:
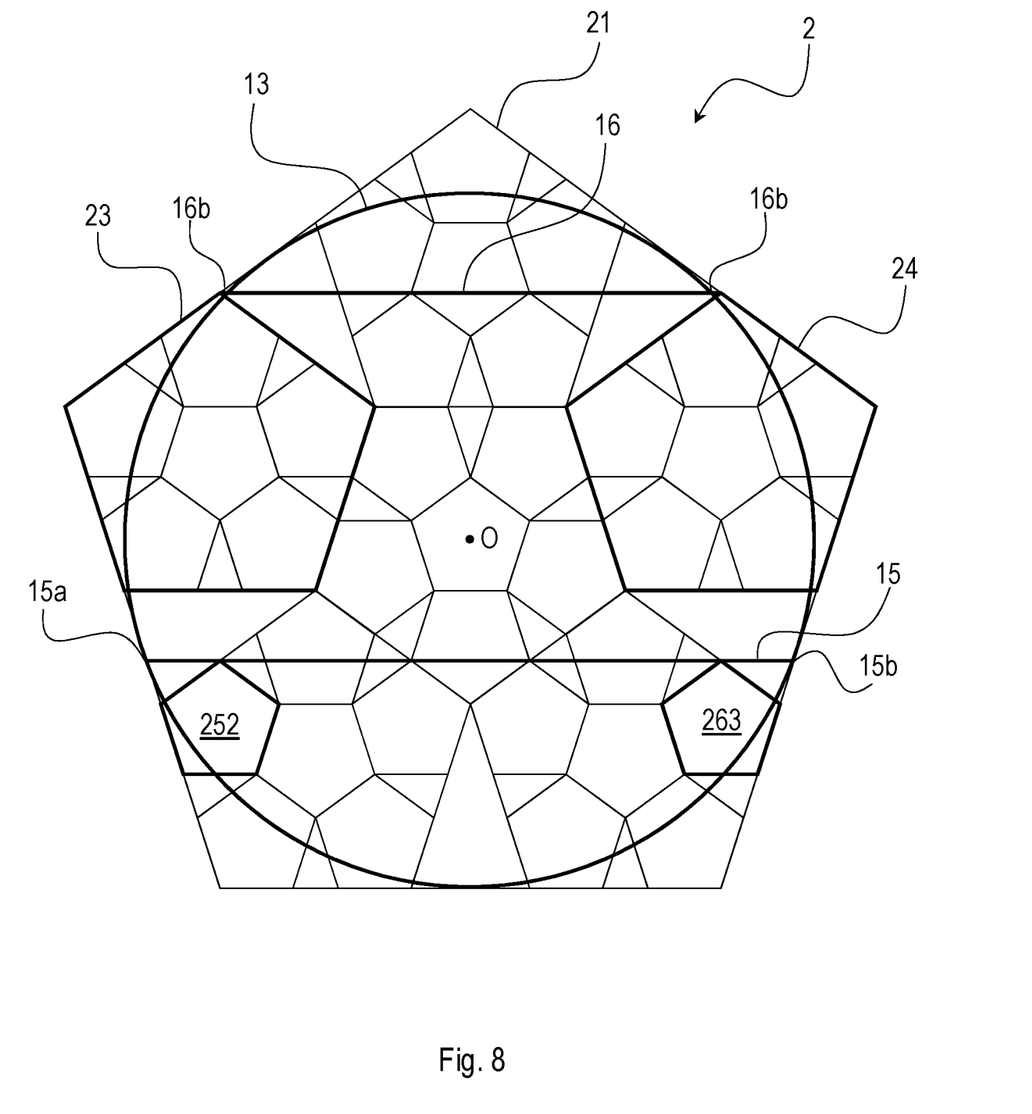
FIGS. 8 to 12 show the combination of the reference circumference in FIG. 4 and the reference grid in FIGS. 5 and 6, to obtain a mitral repair ring according to the invention.

Once the reference grid 2 (step S2) has been generated, the method proceeds with a step S3, in which, as shown in FIG. 8, the reference circumference 13, determined in step S1, is inscribed within the first level pentagon 21 of the reference grid 2.

As shown in detail in FIG. 8, the method then proceeds with a step S4, which consists in combining said reference circumference 13 with a plurality of characteristic measures of the mitral valve 100.

More particularly, the S4 step consists in placing, on the reference grid 2, two characteristic axes of the mitral valve 100, specifically the coaptation axis 15, i.e. the straight line passing through the coaptation point C, and the anteroposterior deformation axis 16, i.e. the straight line passing through the middle point A of the front ring 111.

In particular, the front deformation axis 16 is placed on the reference grid 2 so that it passes through the vertex of the second level side pentagons 23 and 24. The coaptation axis 15 is placed on the reference grid 2 so that it passes through the vertex of the third level side pentagons 252 and 263.

As a result, the front deformation axis 16 intersects the reference circumference 13 at two points, 16a and 16b, respectively, while the coaptation axis 15 intersects the reference circumference 13 at two points, 15a and 15b respectively.

After the placement, on the reference grid 2, of the front deformation 16 and coaptation 15 axes, the stretches 131-134 of the reference circumference 13, indicative of the implanting bases of the anterolateral P1, median P2 and posteromedial P3 portions of the rear valve leaflet 130 and front valve leaflet 120 are determined.

For this purpose, it is assumed that:
the valve ring circumference arcs 110 forming the implanting bases of the anterolateral P1 and posteromedial P3 portions of the rear valve leaflet 130, respectively, have a length equal to that of the radius of the ring valve 110, thus they are intercepted by a first angle $\alpha$ equal to 1 radian ($\cong 57°$);
the valve ring circumference arc 110 forming the implanting base of the median portion P2 of the rear valve leaflet 130 is subtended by a second angle $\beta$, which is in golden ratio with the first angle $\alpha$, so:

$$\beta/\alpha = \phi(\text{Fidia's constant}) = 1.6180339887\ldots$$

the valve ring circumference arc 110 forming the implanting base of the front valve leaflet 120 is subtended by a third angle $\gamma$, which is in golden ratio with the second angle $\beta$, for which:

$$\gamma/\beta = \phi(\text{Fidia's constant}) = 1.6180339887\ldots$$

The Following is Thus Obtained:

$$\alpha = 1\,\text{radiant} \cong 57°$$

$$\beta = \alpha \times \phi = 57° \times 1.6180339887\ldots \cong 92°$$

$$\gamma = \beta \times \phi = 92° \times 1.6180339887\ldots \cong 148°$$

A plurality of radii, i.e. a first radius r1, a second radius r2, a third radius r3, a forth radius r4, a fifth radius r5 and a sixth radius r6 of the reference circumference 13, forming the above angles $\alpha$, $\beta$ and $\gamma$ therebetween, is then placed.

In particular, the first and the second radii r1 and r2 form the $\alpha$ angle therebetween and intercept on the reference circumference 13 one circumference arc 131 which forms the implanting base of the anterolateral portion P1 of the posterior valve leaflet 130; the second and third radii r2 and r3 form the $\beta$ angle therebetween and intercept on the reference circumference 13 a circumference arc 132 which forms the implanting base of the median portion P2 of the rear valve leaflet 130; the third and the forth radii r3 and r4 form the $\alpha$ angle therebetween and intercept on the reference circumference 13 a circumference arc 133 which forms the implanting base of the anteromedial portion P3 of the posterior valve leaflet 130; the fifth and the sixth radii r5 and r6 form the angle $\gamma$ therebetween and intercept on the reference circumference 13 a circumference arc 134 which forms, at least in part, the implanting base of the front valve leaflet 120. Between the first and the sixth radii r1 and r6, and between the fourth and the fifth radii r4 and r5, two areas or circular sectors, respectively 160 and 170, which represent the front CA and rear CP commissures of the mitral valve 100, are delimited.

A circumference arc 17, which passes through the front CA and rear CP commissures and for the coaptation axis 15 is then outlined. This circumference arc 17 represents the coaptation line, i.e. the line of contact between the free edges of the front 120 and rear 130 valve leaflets of the mitral valve 100.

Figure 10:
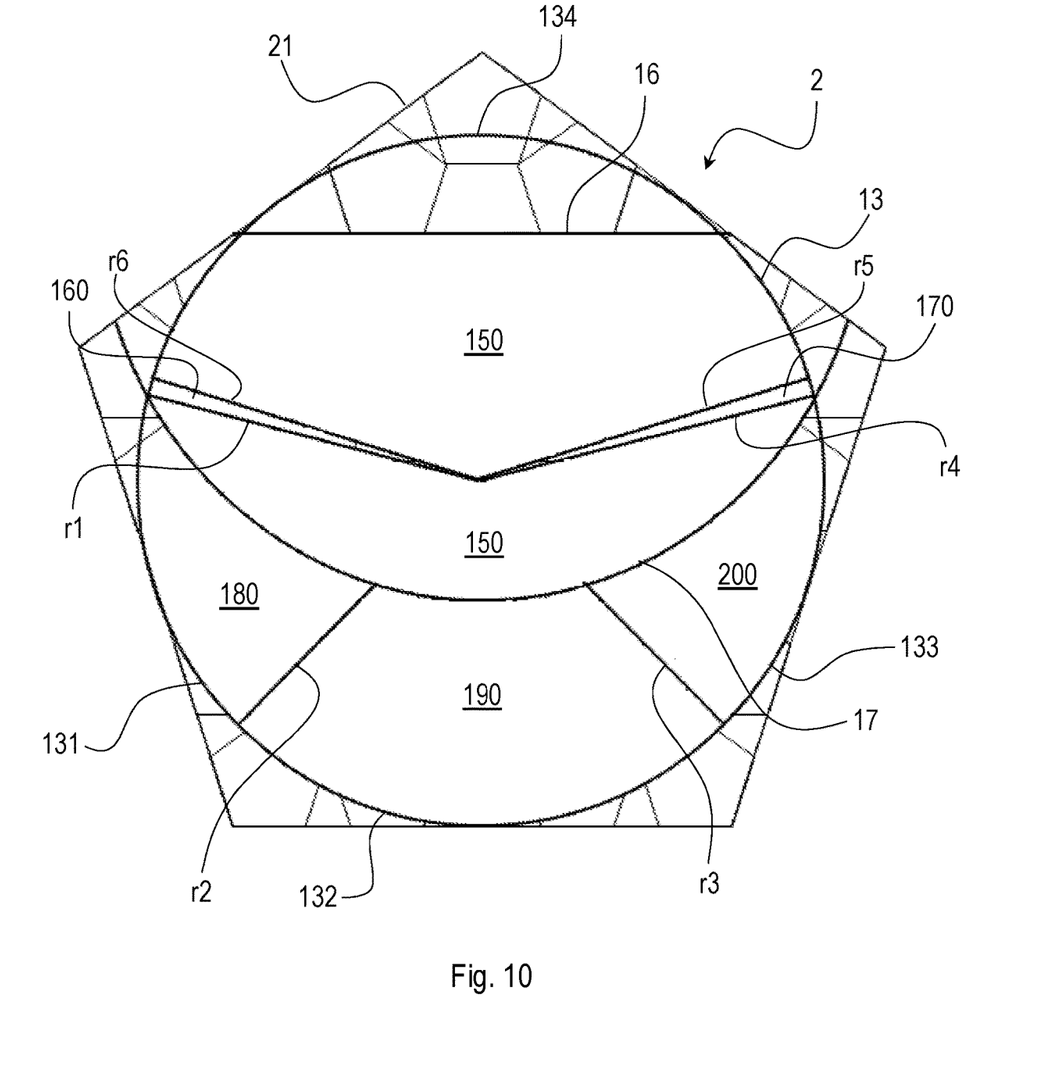

As shown in detail in FIG. 10, following the combination of the reference circumference 13 with the deformation axes front 16 and of coaptation 15, the radii from the first to the sixth r1-r6 forming the angles $\alpha$, $\beta$ and $\gamma$ therebetween, and the circumference arc 17, in the reference grid 2 a plurality of areas 150-190 is defined.

In particular, the area 150 between the circumference arc 134, the front deformation axis 16 and the fifth and the sixth radii r5 and r6, and between the circumference 17 and the first and fourth radii r1 and r4, corresponds to the area of the front leaflet 120; the area 160 between the reference circumference 13 and the first and the sixth radii r1 and r6 corresponds to the area of the front commissure CA; the area 170 between the reference circumference 13 and the fourth and the fifth radii r4 and r5 corresponds to the area of the rear commissure CP; the area 180 between the circumference arc 131, the circumference arc 17 and the second radius r2 corresponds to the anterolateral portion P1 of the rear valve leaflet 130; the area 190 between the circumference arc 132, the circumference arc 17 and the second and the third radius r2 and r3 corresponds to the median portion P2 of the rear valve leaflet 130, and the area 200 between the circumference arc 133, the circumference arc 17 and the third radius r3 corresponds to the posteromedial portion P3 of the rear valve leaflet 130.

A step S5 follows step S4, which consists in the generation of a three-dimensional reference grid 250, from the reference grid 2.

Figure 11:
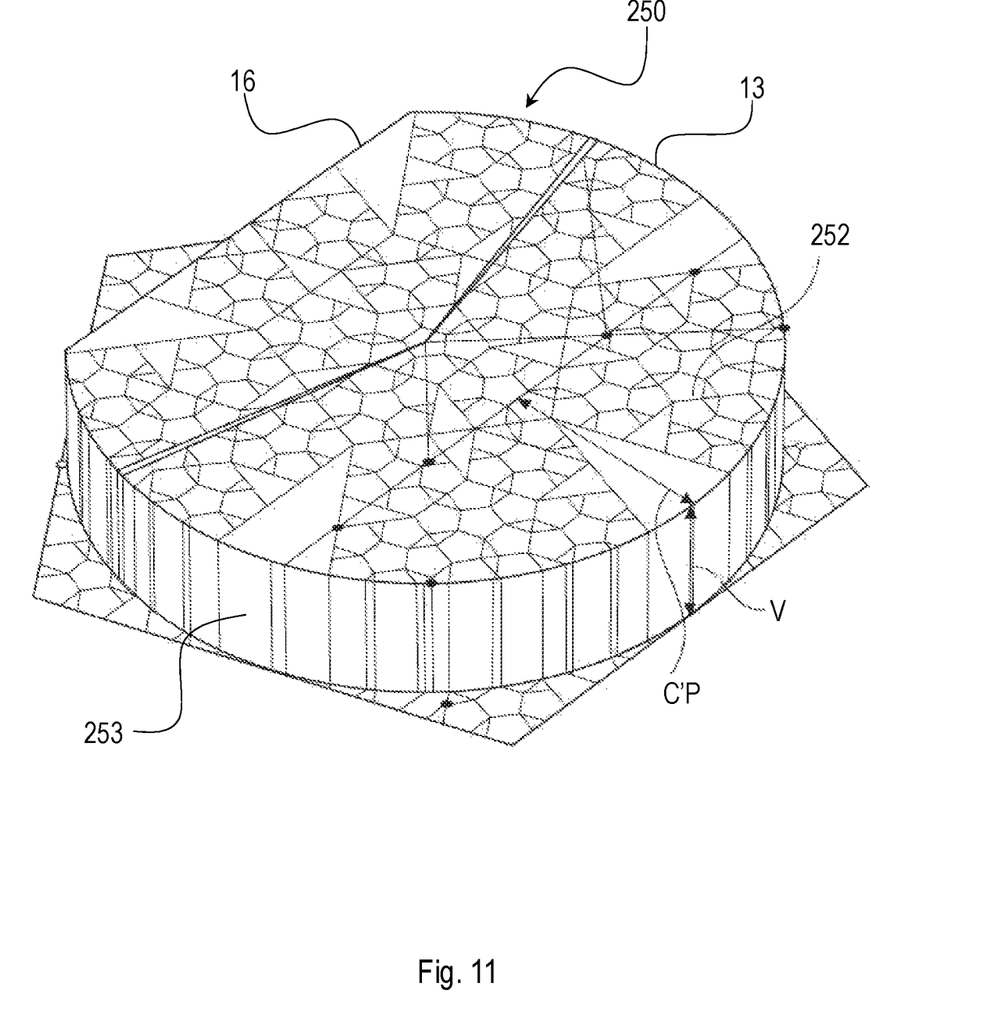

As shown in detail in FIG. 11, the three-dimensional reference grid 250 is obtained by providing a thickness V to the portion of the reference grid 2 occupied by the reference circumference 13 superiorly cut from the front deformation axis 16. The three-dimensional grid 250 thus obtained has therefore the shape of a cylinder longitudinally cut in its front part.

Figure 9:
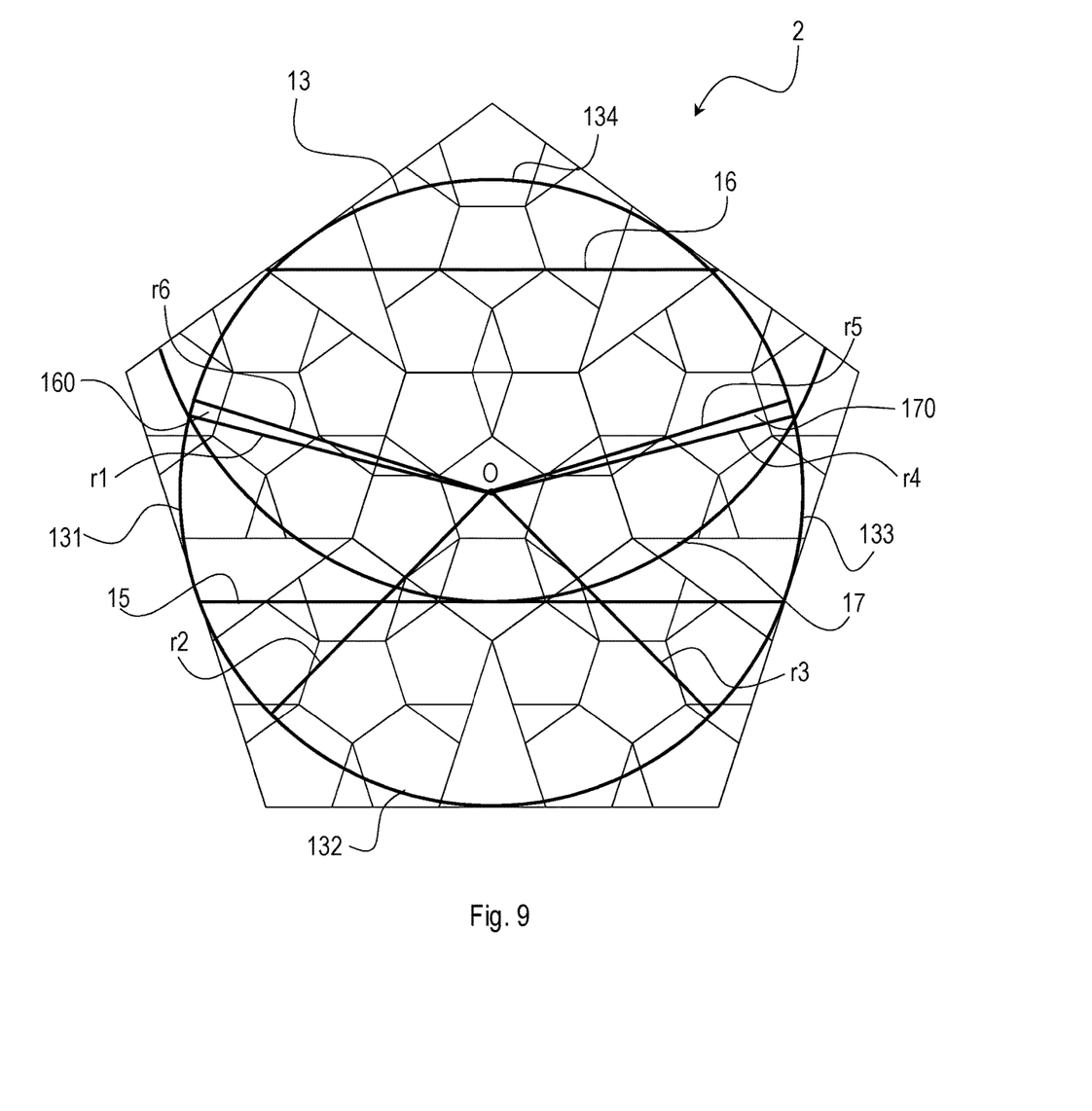

In particular, the thickness V of the three-dimensional reference grid 250 is selected so that it is in golden ratio with the CP stretch, i.e. the maximum height of the area 190 (FIG. 9).

Therefore, the relationship:

$$CP/V = \phi(\text{Fidia's constant}) = 1.6180339887\ldots$$

is valid.

In particular, the thickness V corresponds to the annular height AH (FIG. 3) of the valve ring 110.

The three-dimensional reference grid 250 also has a lower surface 257, an upper surface 258 and a side surface 259.

The step S5 of generating the three-dimensional grid 250 is followed by a step S6, which consists in finding, on the three-dimensional reference grid 250, a plurality of deformation points 300-303 of the reference circumference 13 inscribed in the starting reference grid 2.

Figure 12:
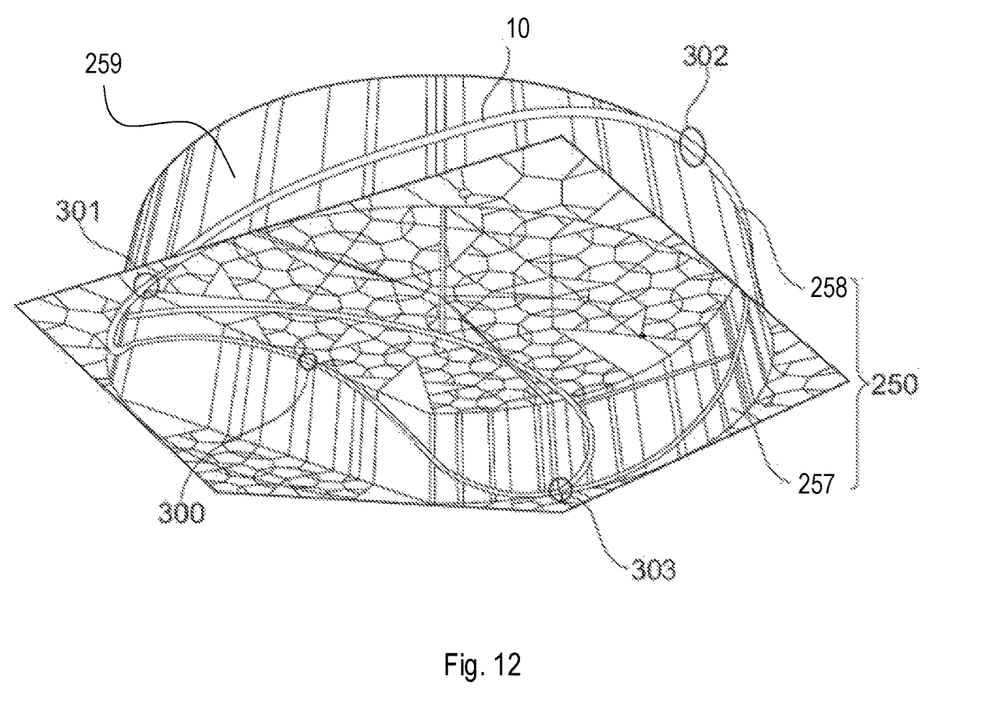

In particular, and as shown in detail in FIG. 12, the following deformation points 300-303 are determined: a first deformation point 300 placed on the upper surface 258 of the three-dimensional grid 250, in the middle of the front deformation axis 16; a second deformation point 301 at the projection, on the lower surface 257 of the three-dimensional grid 250, of a median point identified by the radii r1, r6 which delimit the area 160 of the front commissure CA; a third deformation point 303 at the projection, on the lower surface 257 of the three-dimensional grid 250, of a median point identified by the radii r4 and r5 170 which delimit the area of the rear commissure CP; and a fourth deformation point 302 placed in the upper surface 258 of the three-dimensional grid 250, in the middle of the circumference arc 132 which forms the implanting base of the median portion P2 of the rear valve leaflet 130.

A step S7 follows step S6, during which the reference circumference 13 at the identified deformation points 300-303, in order to obtain a geometric model 10 of a mitral repair ring 10', is deformed.

In particular, the reference circumference 13 is deformed so that the middle part of the area 150, corresponding to the area of the front leaflet 120 of the mitral valve 100, and the middle part of the area 190, corresponding to the median portion P2 of the rear valve leaflet 130 of the mitral valve 100, are in contact with the upper surface 258 of the three-dimensional reference grid 250, while the two areas 160 and 170, respectively corresponding to the areas of the two front CA and rear CP commissures are in contact with the lower surface 257 of the three-dimensional reference grid 250. Thereby, the reference circumference 13 will run perfectly adherent to the side surface 259 of the three-dimensional reference grid 250 and will take the typical saddled shape of the valve ring 110. Furthermore, the coaptation line 17 remains completely resting on the lower surface 257 of the three-dimensional reference grid 250.

Figure 13:
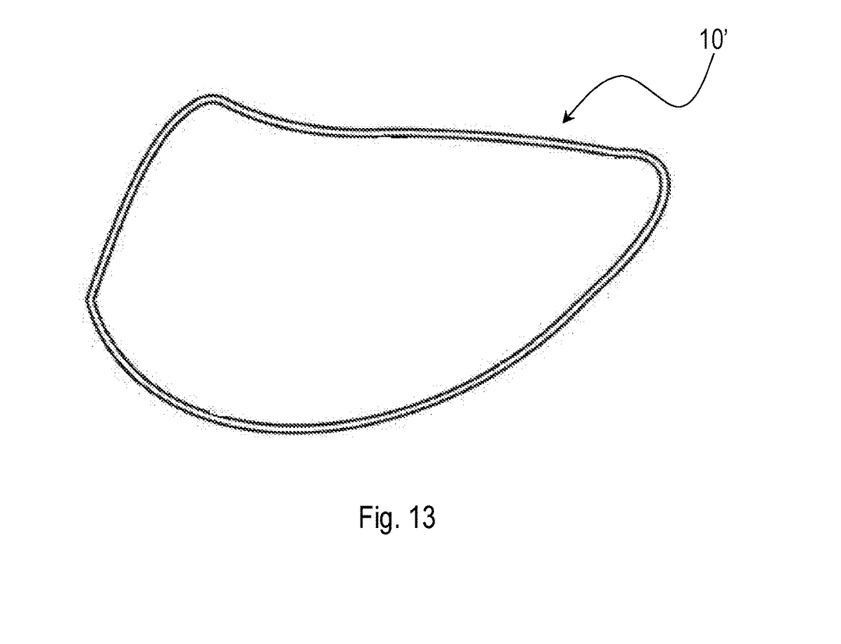
FIG. 13 shows a mitral repair ring obtained by applying the method according to the present invention.

Once the geometric model 10 of the mitral repair ring has been obtained, the generation or production of a mitral repair ring 10' configured according to the geometric model 10 is provided.

The mitral repair ring 10' may be rigid, semi-elastic or elastic.

Preferably, the mitral repair ring 10' is made of a physiologically acceptable material or a material which substantially reduces the risks for adverse reactions or rejection even when provisionally grafted in the human body. For example, the mitral repair ring 10' can be made of rubber, e.g. a silicone rubber.

According to some embodiments, the mitral repair ring 10' has a structure (frame) made of a rigid biocompatible material at least partially coated with a soft non-woven or woven material.

Typically, the mitral repair ring 10' can be used in cardiac surgery to treat a disorder or condition of a mitral valve in a subject in need of the treatment. The treatment may require the replacement of the original mitral valve with a prosthesis or mitral valve implant or the mitral valve repair by resorting to a cardiac surgery technique.

According to some embodiments, the mitral repair ring 10' obtained from the geometric model 10 determined by the method of the invention is temporary or removable, i.e. it is removed when the anatomic impairment of the mitral valve 100 has been adjusted during surgery.

In such a case, the mitral repair ring 10' is rigid and is placed on the valve ring 110 by means of provisional stitches, to open the mitral valve and allow it take natural shape and size when the heart is empty or "deflated". This advantageously allows the surgeon to perform the valve repair with more precise and stable anatomical references. On completion of surgery, when the mitral valve has regained a shape closer as possible to the physiological one, the mitral repair ring 10' can be removed. The temporary repair ring can be sterilized, so it can be reused as another surgical instrument.

Alternatively, the mitral repair ring 10' can be of definitive or implantable type, and therefore does not require to be removed after the surgical repair of the mitral valve 100. In this case, it is a rigid or semi-rigid ring, which is permanently implanted on the ring valve after the repair and serves to stabilize it throughout the patient's life.

From the given description, the features of the method for determining a mitral repair ring and of the mitral repair ring generated by means of such a method of the present invention, are apparent as the advantages thereof are.

Finally, it is apparent that the method for determining a mitral repair ring thus conceived and the corresponding mitral repair ring are susceptible of several modifications and variations, all within the scope of protection of the present invention.

The invention claimed is:

1. A method for producing a mitral repair ring for a mitral valve, said mitral valve comprising a valve ring and a pair of valve leaflets, the method comprising the following steps:
generating a reference circumference indicative of said valve ring;
generating a reference grid;
inscribing said reference circumference in said reference grid;
combining said reference circumference with a plurality of characteristic measures of said mitral valve;
generating a three-dimensional pentagonal reference grid, said generating of the three-dimensional pentagonal reference grid comprising
generating a first level pentagon of a size such as to circumscribe said reference circumference;
generating, within said first level pentagon, a plurality of second level pentagons; and
generating, within each of said second level pentagons, a plurality of third level pentagons;
identifying on said three-dimensional reference grid a plurality of deformation points of said reference circumference;
deforming said reference circumference at said deformation points so as to obtain a geometric model of said mitral repair ring; and
producing said mitral repair ring from the obtained geometric model.

2. The method according to claim 1, wherein said reference circumference is generated from a characteristic measure of said valve ring or said mitral valve.

3. The A method according to claim 2, wherein said characteristic measure of said valve ring is the anteroposterior diameter or an annular height of said valve ring.

4. The method according to claim 2, wherein said characteristic measure of said mitral valve is a maximum height of a rear one of said valve leaflets or a maximum height of valve leaflets of said mitral valve.

5. The method according to claim 1, wherein said step of combining said reference circumference with a plurality of characteristic measures of said mitral valve comprises the steps of:
placing, on said reference grid, a coaptation axis, an anteroposterior deformation axis and a coaptation line; and
placing, on said reference grid, a plurality of radii of said reference circumference, said radii being adapted to intercept, on the reference circumference, circumference arcs forming the implanting bases of an anterolateral portion, a median portion and a posteromedial portion of a rear leaflet and an implanting base of a front leaflet, respectively.

6. The method according to claim 5, wherein anteroposterior deformation axis is placed on said reference grid so that it passes through a vertex of said second level side pentagons and intersects said reference circumference at two points.

7. The method according to claim 6, wherein said coaptation axis is placed on said reference grid so that it passes through a vertex of the third level side pentagons of the second level base pentagons and intersects said reference circumference at two points.

8. The method according to claim 5, wherein said radii comprise a first radius, a second radius, a third radius, a fourth radius, a fifth radius and a sixth radius, wherein said first and second radii and said third and fourth radii form a first angle ($\alpha$) therebetween; said second and third radii form a second angle ($\beta$) therebetween; and said fifth and sixth radii form a third angle ($\gamma$) therebetween.

9. The method according to claim 8, wherein said first, second and third angles are interrelated by the following relations:

$$\beta/\alpha = \Phi$$

$$\gamma/\beta = \Phi$$

where $\Phi$ (Fidia's constant)=1.6180339887.

10. The method according to claim 5, wherein said three-dimensional reference grid is obtained by providing a thickness (V) to the portion of the reference grid occupied by said reference circumference superiorly cut from said anteroposterior deformation axis.

11. The method according to claim 10, wherein said thickness (V) is selected so that it is in golden ratio with a maximum height (C'P) of the rear leaflet of the mitral valve, i.e. the following formula is valid:

$$C'P/V = \Phi$$

where $\Phi$ (Fidia's constant)=1.6180339887.

12. The method according to claim 10, wherein said thickness corresponds to the annular height of said valve ring.

13. The method according to claim 5, wherein said three-dimensional reference grid comprises a lower surface and an upper surface, said deformation points comprise:
a first deformation point placed on said upper surface, in the middle of anteroposterior deformation axis; a second deformation point placed at the projection, on said lower surface, of a median point identified by the first and sixth radii; a third deformation point placed at the projection, on said lower surface, of a median point identified by the fourth and fifth radii; and a fourth deformation point placed, on said upper surface, in the middle of the circumference arc which forms the implanting base of the median portion of the rear leaflet.

14. A mitral repair ring obtained by the method according to claim 1.

15. The mitral repair ring according to claim 14, wherein said ring is rigid, semi-elastic or elastic.

16. The ring according to claim 14, wherein said mitral repair ring is made of a physiologically acceptable material, selected from silicone rubber or biocompatible rigid material coated with a soft non-woven or woven material.

* * * * *